United States Patent
Bartholomäus et al.

(10) Patent No.: US 10,160,719 B2
(45) Date of Patent: *Dec. 25, 2018

(54) PHARMACEUTICAL SALTS

(75) Inventors: Johannes Bartholomäus, Aachen (DE); Heinrich Kugelmann, Aachen (DE)

(73) Assignee: GRUNENTHAL GMBH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/295,242

(22) Filed: Nov. 14, 2011

(65) Prior Publication Data

US 2012/0059066 A1    Mar. 8, 2012

Related U.S. Application Data

(60) Continuation of application No. 12/487,760, filed on Jun. 19, 2009, now abandoned, which is a division of application No. 10/647,882, filed on Aug. 25, 2003, now abandoned, which is a continuation of application No. PCT/EP02/02169, filed on Feb. 28, 2002.

(30) Foreign Application Priority Data

Feb. 28, 2001 (DE) .................................. 101 09 763

(51) Int. Cl.
| | |
|---|---|
| A61K 31/137 | (2006.01) |
| A61K 31/135 | (2006.01) |
| A61P 13/00 | (2006.01) |
| A61P 29/00 | (2006.01) |
| C07C 215/54 | (2006.01) |
| C07C 215/64 | (2006.01) |
| C07C 217/74 | (2006.01) |
| A61K 9/00 | (2006.01) |
| A61K 9/68 | (2006.01) |
| C07C 215/62 | (2006.01) |
| C07C 217/68 | (2006.01) |
| C07D 275/06 | (2006.01) |
| C07D 291/06 | (2006.01) |
| C07D 489/04 | (2006.01) |

(52) U.S. Cl.
CPC .......... *C07C 215/54* (2013.01); *A61K 9/0056* (2013.01); *A61K 9/0058* (2013.01); *A61K 9/0095* (2013.01); *C07C 215/62* (2013.01); *C07C 215/64* (2013.01); *C07C 217/68* (2013.01); *C07C 217/74* (2013.01); *C07D 275/06* (2013.01); *C07D 291/06* (2013.01); *C07D 489/04* (2013.01); *C07B 2200/07* (2013.01); *C07C 2101/14* (2013.01)

(58) Field of Classification Search
None
See application file for complete search history.

(56) References Cited

U.S. PATENT DOCUMENTS

| | | | |
|---|---|---|---|
| 2,538,645 | A | 1/1951 | Hamilton |
| 4,362,730 | A | 12/1982 | Rader et al. |
| 5,733,936 | A | 3/1998 | Buschmann et al. |
| 6,077,822 | A | 6/2000 | Dyrsting et al. |
| 6,090,856 | A | 7/2000 | Sasaki |
| 6,344,558 | B1 | 2/2002 | Buschmann et al. |
| 6,723,343 | B2 | 4/2004 | Kugelmann |
| 7,361,690 | B2 | 4/2008 | Christoph et al. |
| 7,572,463 | B2 | 8/2009 | Bartholomaeus et al. |
| 7,897,173 | B2 | 3/2011 | Ziegler et al. |
| 7,906,141 | B2 | 3/2011 | Ziegler et al. |
| 2001/0029959 | A1 | 10/2001 | Burgard et al. |
| 2001/0041738 | A1 | 11/2001 | Burgard |
| 2002/0176888 | A1 | 11/2002 | Bartholomaeus et al. |
| 2003/0035835 | A1 | 2/2003 | Bartholomaeus et al. |
| 2003/0044464 | A1 | 3/2003 | Ziegler et al. |
| 2003/0158242 | A1 | 8/2003 | Kugelmann |
| 2004/0029878 | A1 | 2/2004 | Christoph et al. |
| 2004/0173224 | A1 | 9/2004 | Burgard et al. |
| 2005/0003002 | A1 | 1/2005 | Ziegler et al. |
| 2005/0065120 | A1 | 3/2005 | Christoph et al. |

FOREIGN PATENT DOCUMENTS

| | | | |
|---|---|---|---|
| DE | 3 639 902 | | 1/1988 |
| DE | 3 639 903 | | 1/1988 |
| DE | 3 639 901 | | 6/1988 |
| DE | 44 26 245 | | 2/1996 |
| DE | 19 525 137 | | 1/1997 |
| DE | 19 547 766 | | 6/1997 |
| DE | 196 01 744 | | 7/1997 |
| DE | 19940740 | A1 * | 3/2001 ........... A61K 9/2081 |
| DE | 199 47 747 | | 4/2001 |
| DE | 10013712 | A1 | 9/2001 |
| EP | 0 061 654 | | 10/1982 |
| EP | 0 693 475 | | 1/1996 |

(Continued)

OTHER PUBLICATIONS

STN online, file DRUGU, Acc. No. 1992-09870, (Plagge, Krankenhauspharmazie (1991), vol. 12, No. 111, pp. 488-491), Abstract.*
Gennaro, Ed., Remington's Pharmaceutical Sciences (17th Ed., 1985), pp. 1604, 1644, 1645, 1650-1654.*
Plagge, Tramadol Drops:Preparation and Analytics, Pharmacy of the Central Clinic Augsburg (1991), vol. 12, No. 11, pp. 488-492.*
List of Pharmaceutical Substances, 12th Edition, T-Tril, ABDATA, Pharma-Daten-Service, p. 348 and 3661-3662, (2000).
Ullmann's Encyclopedia of Industrial Chemistry, 6th Edition, Wiley-VCH, Weinheim (1998) ISBN: 3-527-20164, pp. 1-3.

(Continued)

*Primary Examiner* — Sue X Liu
*Assistant Examiner* — Frank Choi
(74) *Attorney, Agent, or Firm* — Norris McLaughlin, P.A.

(57) ABSTRACT

The invention relates to pharmaceutical salts comprised of a pharmaceutical active substance and of at least one sugar substitute, to medicaments containing these salts, and to the use of these salts for producing medicaments.

10 Claims, No Drawings

(56) References Cited

FOREIGN PATENT DOCUMENTS

| | | |
|---|---|---|
| EP | 0 799 819 | 10/1997 |
| EP | 1 136 487 | 9/2001 |
| EP | 1 270 580 | 1/2003 |
| RU | 98104277 A1 | 1/2000 |
| RU | 2156129 C1 | 9/2000 |
| WO | 97/06824 A2 | 2/1997 |
| WO | 97/33877 A1 | 9/1997 |
| WO | 98 46216 A1 | 4/1998 |
| WO | 00 12067 | 3/2000 |
| WO | 01 15667 | 3/2001 |
| WO | 01 15681 A1 | 3/2001 |
| WO | 01 15682 A1 | 3/2001 |
| WO | 01 15683 A1 | 3/2001 |
| WO | 02 43715 A2 | 6/2002 |

OTHER PUBLICATIONS

Ward et al., Eng. Phys. Sci. Res. Council, 208-211 (2003).
Banerjee et al., Crystal Growth Des., 5(6): 2299-2309 (2005).
Almarsson et al., Chem. Commun., 1889-1896 (2004).
Bhatt et al., Chem. Commun., 1073-1075 (2005).
E. Friderichs, T. Christoph, H. Buschman, Pharmaceuticals, J.L. McGuire, Band 2, S. 341-434, Wiley VHC, Weinheim "Analgesics and Antipyretics".
Fukutaro Ugai et al, "On the Derivatives of Saccharin Saldt of Main Alkaoids in Opium", Mag. for Pharma. Jap., Pharmaceutical Community, 1961, vol. 81, p. 151-152.

\* cited by examiner

PHARMACEUTICAL SALTS

The present invention relates to pharmaceutical salts of an active compound and at least one sugar substitute, medicaments comprising these salts, and the use of these salts for the production of medicaments.

On oral administration, a large number of pharmaceutical active compounds having excellent activity lead to a strongly bitter, often nauseating taste sensation in the patient. In some patients, lack of adherence to the dosage instructions and a lack of acceptance of the corresponding medicaments which release such an active compound as early as during taking result from this negative taste experience.

The formulation of pharmaceutical active compounds having very good water solubility to give medicaments frequently causes problems in pharmaceutical practice. Thus the preparation of pharmaceutical forms having controlled release is often made difficult on account of the very good water solubility of active compound salts. A delaying of the release of these active compounds can in fact be achieved, for example, by coating the pharmaceutical forms with release-delaying film coatings. This manner of delaying the release, however, is associated with a relatively high outlay, since release-delaying film coatings from aqueous coating systems are frequently only an inadequate diffusion barrier for active compounds having very good water solubility. The preparation of these delayed-release active compound preparations therefore requires relatively complicated coating processes with multilayer films. If such release-delaying coatings are applied from organic solvents, the environmental and solvent residue problems associated therewith additionally make the preparation of appropriate preparations more expensive.

It was therefore the object of the present invention to make available pharmaceutical combinations of active compounds which have no bitter taste. Preferably, the corresponding active compounds should be simpler to formulate and their release should be more effectively delayed.

According to the invention, this object is achieved by the provision of pharmaceutical salts, i.e. physiologically tolerable salts, from a pharmaceutical active compound and at least one sugar substitute.

The present invention therefore relates to pharmaceutical salts of a pharmaceutical active compound and at least one sugar substitute, the respective pharmaceutical salts of a sugar substitute and tramadol, (+)-tramadol, (−)-tramadol, (+)-demethyltramadol and (−)-demethyltramadol being excepted.

In a preferred embodiment of the present invention, the solubility of the pharmaceutical salts according to the invention in water is ≤250 mg/ml of water, preferably ≤200 mg/ml, particularly preferably ≤150 mg/ml, very particularly preferably ≤100 mg/ml. This can also be seen in particular in the fact that the water solubility of the pharmaceutical salts according to the invention compared with the water solubility of the best water-soluble salt of the corresponding active compound according to Pharmazeutische Stoffliste [Pharmaceutical Substance List], 12th edition ABDATA Pharma-Daten-Service, 65735 Eschborn/Taunus, is preferably lowered by at least 50%, preferably by at least 65%, particularly preferably by at least 75%, very particularly preferably by at least 85%, compared with the corresponding hydrochloride. The corresponding literature description is hereby inserted as a reference and is thus regarded as part of the disclosure.

According to the invention, suitable sugar substitutes are all sugar substitutes which can form a salt with the respective pharmaceutical active compound with formation of an at least singly negatively charged form. According to the invention, pharmaceutical salts are also included in which the pharmaceutical active compound has two or more different sugar substitutes as salt components. Preferably, the pharmaceutical salts according to the invention contain saccharin, cyclamate or acesulfam, particularly preferably saccharin, as salt-forming sugar substitutes.

According to the invention, suitable active compounds are all pharmaceutical active compounds which can form a salt in anionic form with the respective sugar substitute(s) with formation of an at least singly positively charged form.

In a further preferred embodiment of the present invention, the salt-forming active compound in the pharmaceutical salt according to the invention is selected from the group consisting of the salt-forming analgesics, antiobesity agents, analeptics, antihypoxemics, antirheumatics, opioid antagonists, anthelmintics, antiallergics, antiarrhythmics, antibiotics, antidementives (nootropics), antidiabetics, antiemetics, antivertiginous agents, antiepileptics, antihypertensives, antihypotensives, antimycotics, antiinflammatories, antitussives, expectorants, arteriosclerosis agents, β-receptor blockers, calcium channel blockers, broncholytics, antiasthmatics, cholinergics, diuretics, circulation-promoting agents, weaning agents, geriatrics, hypnotics, sedatives, immunomodulators, oral therapeutics, pharyngeal therapeutics, coronary agents, hypolipidemics, local anesthetics, neural therapeutics, gastric agents, intestinal agents, migraine agents, muscle relaxants, anesthetics, neuropathy preparations, ophthalmologicals, otologicals, Parkinson agents, psychopharmaceuticals, rhinologicals, sinusitis agents, spasmolytics, platelet aggregation inhibitors, tuberculosis agents, urologicals and cytostatics. Particularly preferably, the salt-forming active compound is selected from the group consisting of the salt-forming analgesics, analeptics, antihypoxemics, antiallergics, antiarrhythmics, antiemetics, antivertiginous agents, antihypertensives, antihypotensives, antitussives, expectorants, β-receptor blockers, calcium channel blockers, ophthalmologicals, otologicals, spasmolytics and urologicals. Very particularly preferably, the salt-forming active compound is selected from the group consisting of the salt-forming analgesics, tramadol, (+)-tramadol, (−)-tramadol, (+)-demethyltramadol and (−)-demethyltramadol being excepted.

If the pharmaceutical active compound is a salt-forming analgesic, it is preferably a salt-forming opioid or a salt-forming opioid analog, such as disclosed in E. Friderichs, T. Christoph, H. Buschmann, "Analgesics, and Antipyretics"; Ullmann's Encyclopedia of Industrial Chemistry, Sixth Edition on CD-ROM, Wiley-VCH, Weinheim, 2000 or in Pharmaceuticals, J. L. McGuire (Editor), Analgesics and Antipyretics, Volume 2, pages 341-434, Wiley-VCH, Weinheim or ephedrine, chloroquine, lidocaine, ethaverine, preglumetacin or triflupromazine. The corresponding disclosures are hereby inserted as a reference and are thus regarded as part of the present disclosure. Particularly preferably, the salt-forming analgesic is selected from the group consisting of morphine, codeine, ethylmorphine, diacetylmorphine, dihydrocodeine, etorphine, hydrocodone, hydromorphone, levorphanol, oxycodone, oxymorphone, pethidine, ketobemidone, fentanyl, alfentanil, remifentanil, sufentanil, levomethadone, levomethadyl, dextro-moramide, dextropropoxyphene, diphenoxylate, piri-tramide, tilidine, buprenorphine, butorphanol, dezozine, meptazinol, nalbuphine, nalorphine, pentazo-cine, flupirtin and nefopam or a representative of the group consisting of ephedrine, chloroquine, lidocaine, ethaverine, preglumetacin and triflupromazine. Very particularly preferably, the salt-forming analgesic is a salt-forming opioid or opioid analog selected from the group consisting of morphine, codeine, hydrocodone, hydromorphone, oxycodone, tilidine, fentanyl and buprenorphine.

Likewise preferably, the salt-forming active compound is a salt-forming compound of 1-phenyl-3-dimethylaminopropane compounds of the general formula I

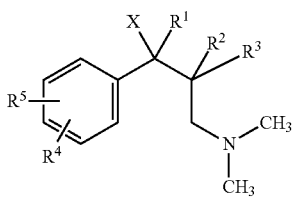

I in which in each case

X is OH, F, Cl, H or an $OCOR^6$ group, $R^1$ is a $C_{1-4}$-alkyl group, $R^2$ is H or a $C_{1-4}$-alkyl group and $R^3$ is H or a straight-chain $C_{1-4}$-alkyl group or the radicals $R^2$ and $R^3$ together form a $C_{4-7}$-cycloalkyl radical, and if $R^5$ is H, $R^4$ is meta-O—Z where Z is H, $C_{1-3}$-alkyl PO(O—$C_{1-4}$-alkyl)$_2$, CO(O$C_{1-5}$-alkyl), CONH—$C_6H_4$—($C_{1-3}$-alkyl) CO—$C_6H_4$—$R^7$, where $R^7$ is ortho-OCO$C_{1-3}$-alkyl or meta- or para-CH$_2$N($R^8$)$_2$ where $R^8$ is $C_{1-4}$-alkyl or 4-morpholino, or $R^4$ is meta-S—$C_{1-3}$-alkyl, meta-Cl, meta-F, meta-CR$^9$R$^{10}$R$^{11}$ where $R^9$, $R^{10}$ and $R^{11}$ are H or F, ortho-OH, ortho-O—$C_{2-3}$-alkyl, para-F or para-CR$^9$R$^{10}$R$^{11}$ where $R^9$, $R^{10}$, $R^{11}$ are H or F, or if $R^5$ is para-Cl, —F, —OH or —O—$C_{1-3}$-alkyl, $R^4$ is meta-Cl, —F, —OH or —O—$C_{1-3}$-alkyl, or $R^4$ and $R^5$ together are 3,4-OCH=CH— or 3,4-OCH=CHO—, $R^6$ is $C_{1-3}$-alkyl, in the form of their possible stereoisomers as racemates or diastereomerically pure enantiomers or in the form of mixtures of enantiomers, in which the respective enantiomers are present in nonequimolar amounts.

Preferred is a salt-forming compound of 1-phenyl-3-dimethylaminopropane compounds of the general formula I in which X is OH, F, Cl or H, $R^1$ is a $C_{1-4}$-alkyl group, $R^2$ is H or CH$_3$ and $R^3$ is H or CH$_3$ and if $R^5$ is H, $R^4$ is meta-O—$C_{1-3}$-alkyl, meta-OH, meta-S—$C_{1-3}$-alkyl, meta-F, meta-Cl, meta-CH$_3$, meta-CF$_2$H, meta-CF$_3$ or para-CF$_3$ or if $R^5$ is a para-Cl or —F, $R^4$ is meta-Cl or —F, or $R^4$ and $R^5$ together are 3,4-OCH=CH—.

Particularly preferred is a salt-forming compound of 1-phenyl-3-dimethylaminopropane compounds of the general formula I in which the radicals $R^2$ and $R^3$ have different meanings and which are present in the form of their diastereomers having the configuration Ia

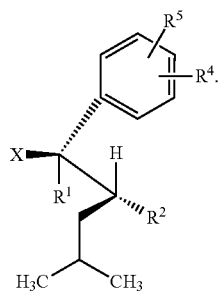

Ia

Very particularly preferred is a salt-forming compound of 1-phenyl-3-dimethylaminopropane compounds of the general formula I, selected from the group consisting of
(1RS,2RS)-3-(3-dimethylamino-1-hydroxy-1,2-dimethylpropyl)phenol,
(−)-(1R,2R)-3-(3-dimethylamino-1-ethyl-2-methylpropyl)-phenol,
(+)-(1S,2S)-3-(3-dimethylamino-1-ethyl-2-methylpropyl)-phenol,
(2RS,3RS)-1-dimethylamino-3-(3-methoxyphenyl)-2-methyl-pentan-3-ol,
(−)-(1S,2S)-3-(3-dimethylamino-1-ethyl-1-fluoro-2-methylpropyl)phenol,
(+)-(1R,2R)-3-(3-dimethylamino-1-hydroxy-1,2-dimethylpropyl)phenol,
(+)-(2R,3R)-1-dimethylamino-3-(3-methoxyphenyl)-2-methylpentan-3-ol and
(−)-(2S,3S)-1-dimethylamino-3-(3-methoxyphenyl)-2-methylpentan-3-ol.

The preparation of the salt-forming compounds of 1-phenyl-3-dimethylaminopropane compounds of the general formula I and, if appropriate, the separation into the pure optical antipodes can be carried out according to customary methods known to the person skilled in the art. Preferably, the preparation and, if appropriate, the separation is carried out as described in DE-A-4426245 or EP 0 693 475 B1, which are hereby inserted as reference and are thus regarded as part of the disclosure.

In a further preferred embodiment of the present invention, the pharmaceutical salt according to the invention contains as a salt-forming active compound a salt-forming compound of 6-dimethylaminomethyl-1-phenylcyclohexane compounds of the general formula II,

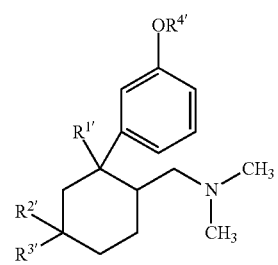

II in which in each case $R^{1'}$ is H, OH, Cl or F, preferably H, OH or F, $R^{2'}$ and $R^{3'}$ are identical or different and are H, $C_{1-4}$-alkyl, benzyl, CF$_3$, OH, OCH$_2$—$C_6H_5$, O—$C_{1-4}$-alkyl, Cl or F with the proviso that at least one of the radicals $R^{2'}$ or $R^{3'}$ is H, R4' is H, CH₃, PO(O—C₁₋₄-alkyl)₂, CO(OC₁₋₅-alkyl), CO—NH—C₆H₄—C₁₋₃-alkyl, CO—C₆H₄—R5', CO—C₁₋₅-alkyl, CO—CHR6'—NHR7' or an unsubstituted or substituted pyridyl, thienyl, thiazoyl [sic] or phenyl group, R5' is OC(O)C₁₋₃-alkyl in the ortho-position or CH₂—N(R8')₂ in the meta- or para-position, where R8' is C₁₋₄-alkyl or both radicals R8' together with N are the 4-morpholino radical, and R6' and R7' are identical or different and are H or C₁₋₆-alkyl, with the proviso that if both radicals R2' and R3' are H, R4' is not CH₃ if R1' is H, OH or Cl or R4' is not H if R1' is OH, in the form of their possible stereoisomers as racemates or diastereomerically pure enantiomers or in the form of mixtures of enantiomers, in which the respective enantiomers are present in nonequimolar amounts.

Preferred are salt-forming compounds of 6-dimethylaminomethyl-1-phenylcyclohexane compounds of the general formula II, which are present in the configuration as in the general formula IIa,

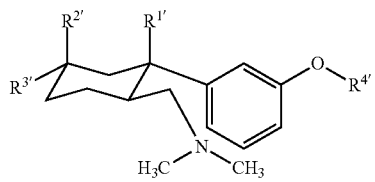

in which the phenyl ring and the dimethylaminomethyl group are in each case arranged in an equatorial position to one another.

Particularly preferred is a salt-forming compound of 6-dimethylaminomethyl-1-phenylcyclohexane compounds of the general formula II selected from the group consisting of (−)-(1R,2R)-3-(2-dimethylaminomethylcyclohexyl)phenol, (1RS,3RS,6RS)-6-(dimethylaminomethyl)-1-(3-methoxyphenyl)cyclohexane-1,3-diol and (1RS,3RS,6RS)-6-(dimethylaminomethyl)-1-(3-hydroxyphenyl)cyclohexane-1,3-diol.

The preparation of the salt-forming compounds of 6-dimethylaminomethyl-1-phenylcyclohexane compounds of the general formula II and, if appropriate, the separation into the optically pure antipodes can be carried out according to customary methods known to the person skilled in the art. Preferably, the preparation and, if appropriate, the separation are carried out as described in DE-A-19525137. The corresponding literature description is hereby inserted as reference and is thus regarded as part of the disclosure.

In a further preferred embodiment of the present invention, the pharmaceutical salt according to the invention contains as a salt-forming active compound a salt-forming compound of 1-phenyl-2-dimethylamino-methylcyclohexan-1-ol compounds of the general formula III,

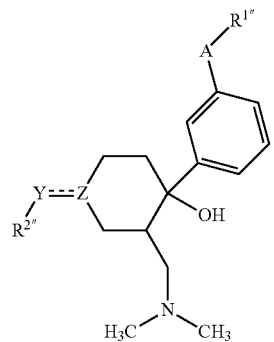

in which in each case

A is O or S,

R1" is H, C₁₋₆-alkyl, C₂₋₆-alkenyl, C₅₋₇-cycloalkyl or halogenated C₁₋₆-alkyl, the group

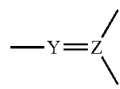

is the group

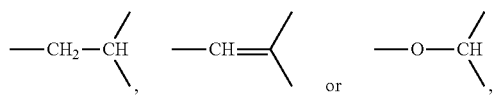

R2" is C₁₋₆-alkyl, C₂₋₆-alkenyl, C₅₋₇-cycloalkylmethyl, substituted or unsubstituted phenyl or substituted or unsubstituted benzyl, in the form of their possible stereoisomers as racemates or diastereomerically pure enantiomers or in the form of mixtures of enantiomers, in which the respective enantiomers are present in nonequimolar amounts.

Preferred are salt-forming compounds of 1-phenyl-2-dimethylaminomethylcyclohexan-1-ol compounds of the general formula III, in which R1" is H, C₁₋₄-alkyl, 2'-methyl-2'-propenyl, cyclopentyl or fluoroethyl, with the proviso that R1" is C₁₋₄-alkyl if A is S, R2" is C₁₋₄-alkyl, C₂₋₄-alkenyl, cyclopentylmethyl, phenyl, C₁₋₄-alkoxyphenyl, benzyl, C₁₋₄-alkylbenzyl, mono- or dihalogenated phenyl or mono- or dihalogenated benzyl.

Particularly preferred are salt-forming compounds of 1-phenyl-2-dimethylaminomethylcyclohexan-1-ol compounds of the general formula III, in which R1" is H, methyl, ethyl, isopropyl, 2'-methyl-2'-propenyl, cyclopentyl or fluoroethyl, with the proviso that R1" is methyl if A is S, R2" is methyl, propyl, 2'-methylpropyl, allyl, 2'-methyl-2'-propenyl, cyclopentylmethyl, phenyl, 3-methoxyphenyl, benzyl, 4-tert-butylbenzyl, 4-chlorobenzyl, 4-fluorobenzyl or 3,4-dichlorobenzyl.

Very particularly preferred are salt-forming compounds of 1-phenyl-2-dimethylaminomethylcyclohexan-1-ol compounds of the general formula III which are present in the configuration of the formula IIIa,

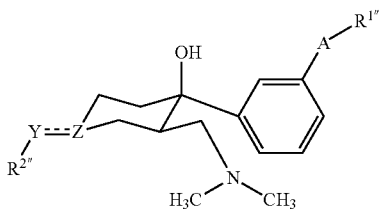

IIIa in which the phenyl ring and the dimethylaminomethyl group are in each case arranged in an equatorial position to one another.

Most preferred is the salt-forming compound of 1-phenyl-2-dimethylaminomethylcyclohexan-1-ol compounds of the general formula III selected from the group consisting of
(+)-(1R,2R,4S)-2-(dimethylaminomethyl)-4-(4-fluorobenzyloxy)-1-(3-methoxyphenyl)cyclohexanol,
(+)-(1R,2R,4S)-2-dimethylaminomethyl-4-(4-chlorobenzyloxy)-1-(3-methoxyphenyl)cyclohexanol and
(+)-(1R,2R,4S)-3-[2-dimethylaminomethyl-4-(4-fluorobenzyloxy)-1-hydroxycyclohexyl]phenol.

The preparation of the salt-forming compounds of 1-phenyl-2-dimethylaminomethylcyclohexan-1-ol compounds of the general formula III and, if appropriate, the separation into the optically pure antipodes can be carried out according to customary methods known to the person skilled in the art. Preferably, the preparation and, if appropriate, the separation are carried out as described in DE-A-19547766, which is hereby inserted as reference and is thus regarded as part of the disclosure.

In a further preferred embodiment of the present invention, the pharmaceutical salt contains as a salt-forming active compound a salt-forming compound of dimethyl-(3-arylbut-3-enyl)amine compounds of the general formula IV, in which [sic]

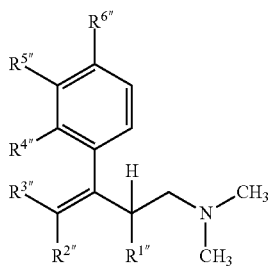

IV the radical $R^{1'''}$ is $C_{1-5}$-alkyl and $R^{2'''}$ is H or $C_{1-5}$-alkyl or $R^{1'''}$ and $R^{2'''}$ together are —$(CH_2)_{2-4}$—, —$(CH_2)_2$—$CHR^{7'''}$— or —$CH_2$—$CHR^{7'''}$—$CH_2$—, $R^{3'''}$ is H or $C_{1-5}$-alkyl, $R^{4'''}$ is H, OH, $C_{1-4}$-alkyl, O—$C_{1-4}$-alkyl, O-benzyl, $CF_3$, O—$CF_3$, Cl, F or $OR^{8'''}$, $R^{5'''}$ is H, OH, $C_{1-4}$-alkyl, O—$C_{1-4}$-alkyl, O-benzyl, $CHF_2$, $CF_3$, O—$CF_3$, Cl, F or $OR^{8'''}$ and $R^{6'''}$ is H, OH, $C_{1-4}$-alkyl, O—$C_{1-4}$alkyl, O-benzyl, $CF_3$, O—$CF_3$, Cl, F or $OR^{8'''}$, with the proviso that two of the radicals $R^{4'''}$, $R^{5'''}$ or $R^{6'''}$ are H, or $R^{4'''}$ and $R^{5'''}$ together are —CH=C($R^{9'''}$)—O— or —CH=C($R^{9'''}$)—S—, with the proviso that $R^{6'''}$ is H, or $R^{5'''}$ and $R^{6'''}$ together are —CH=CH—C($OR^{10'''}$)=CH—, with the proviso that $R^{4'''}$ is H, $R^{7'''}$ is $C_{1-8}$-alkyl, $C_{3-8}$-cycloalkyl, O—$C_{1-4}$-alkyl, O-benzyl, $CF_3$, Cl or F, $R^{8'''}$ is CO—$C_{1-5}$-alkyl, PO(O—$C_{1-4}$-alkyl)$_2$, CO—$C_6H_4$—$R^{11'''}$, CO(O—$C_{1-5}$-alkyl), CO—$CHR^{12'''}$—$NHR^{13'''}$, CO—NH—$C_6H_3$—$(R^{14'''})_2$ or an unsubstituted or substituted pyridyl, thienyl, thiazoyl [sic] or phenyl group, $R^{9'''}$ is H or $C_{1-4}$-alkyl, $R^{10'''}$ is H or $C_{1-3}$-alkyl, $R^{11'''}$ is OC(O)—$C_{1-3}$-alkyl in the ortho-position or $CH_2$—N—$(R^{15'''})_2$ in the meta- or para-position, where $R^{15'''}$ is $C_{1-4}$-alkyl or both radicals $R^{15'''}$ together with N form the 4-morpholino radical, $R^{12'''}$ and $R^{13'''}$ are identical or different and are H, $C_{1-6}$-alkyl or $C_{3-8}$-cycloalkyl or $R^{12'''}$ and $R^{13'''}$ together are —$(CH_2)_{3-8}$—, $R^{14'''}$ is H, OH, $C_{1-7}$-alkyl, O—$C_{1-7}$-alkyl, phenyl, O-aryl, $CF_3$, Cl or F, with the proviso that the two radicals $R^{14'''}$ are identical or different, in the form of their possible stereoisomers as racemates or diastereomerically pure enantiomers or in the form of mixtures of enantiomers, in which the respective enantiomers are present in nonequimolar amounts.

Preferred are salt-forming compounds of dimethyl-(3-arylbut-3-enyl)amine compounds of the general formula IV, in which $R^{1'''}$ is $C_{1-3}$-alkyl and $R^{2'''}$ is H or $C_{1-3}$-alkyl, or $R^{1'''}$ and $R^{2'''}$ together are —$(CH_2)_{2-4}$— or —$(CH_2)_2$—$CHR^{7'''}$, $R^{3'''}$ is H or $C_{1-3}$-alkyl, $R^{4'''}$ is H, OH, $CF_3$, Cl, F or $OR^{8'''}$, $R^{5'''}$ is H, OH, $C_{1-4}$-alkyl, O—$C_{1-4}$-alkyl, O-benzyl, $CHF_2$, $CF_3$, Cl, F or $OR^{8'''}$ and $R^{6'''}$ is H, OH, O—$C_{1-4}$-alkyl, O-benzyl, $CF_3$, Cl, F or $OR^{8'''}$, with the proviso that two of the radicals $R^{4'''}$, $R^{5'''}$ or $R^{6'''}$ are H, or $R^{4'''}$ and $R^{5'''}$ together are —CH=C($R^{9'''}$)—O— or —CH=C($R^{9'''}$)—S—, with the proviso that $R^{6'''}$ is H, or $R^{5'''}$ and $R^{6'''}$ together are —CH=CH—C($OR^{10'''}$)=CH—, with the proviso that $R^{4'''}$ is H, and $R^{7'''}$ is $C_{1-4}$-alkyl, $CF_3$, Cl or F.

Particularly preferred are salt-forming compounds of dimethyl-(3-arylbut-3-enyl)amine compounds of the general formula IV, in which $R^{1'''}$ is $CH_3$ or $C_3H_7$ and $R^{2'''}$ is H, $CH_3$ or $CH_2CH_3$, or $R^{1'''}$ and $R^{2'''}$ together are —$(CH_2)_{2-3}$— or —$(CH_2)_2$—$CHR^{7'''}$, $R^{3'''}$ is H, $CH_3$ or $CH_2CH_3$, $R^{4'''}$ is H or OH, $R^{5'''}$ is H, OH, $OCH_3$, $CHF_2$ or $OR^{8'''}$ and $R^{6'''}$ is H, OH or $CF_3$, with the proviso that two of the radicals $R^{4'''}$, $R^{5'''}$ or $R^{6'''}$ are H, or $R^{4'''}$ and $R^{5'''}$ together are —CH=C($CH_3$)—S—, with the proviso that $R^{6'''}$ is H, or $R^{5'''}$ and $R^{6'''}$ together are —CH=CH—C(OH)=CH—, with the proviso that $R^{4'''}$ is H, and $R^{8'''}$ is CO—$C_6H_4$—$R^{11'''}$ where $R^{11'''}$ is OC(O)—$C_{1-3}$-alkyl in the ortho-position.

Very particularly preferred are salt-forming compounds of dimethyl-(3-arylbut-3-enyl)amine compounds of the general formula IV, in which $R^{1'''}$ is $CH_3$ and $R^{2'''}$ is H or $CH_3$ or $R^{1'''}$ and $R^{2'''}$ together are —$(CH_2)_{2-3}$— or —$(CH_2)_2$—$CH(CH_3)$—, $R^{3'''}$ is H or $CH_3$, $R^{4'''}$ is H, $R^{5'''}$ is OH or $OR^{8'''}$, $R^{6'''}$ is H, and $R^{8'''}$ is CO—$C_6H_4$—$R^{11'''}$ where $R^{11'''}$ is OC(O)—$CH_3$ in the ortho-position.

Most preferred is the salt-forming compound of dimethyl-(3-arylbut-3-enyl)amine compounds of the general formula IV trans-(−)-(1R)-3-[1-(2-dimethylamino-1-methylethyl) propenyl]phenol.

The preparation of the salt-forming compounds of dimethyl-(3-arylbut-3-enyl)amine compounds of the general formula IV and, if appropriate, the separation into the optically pure antipodes can be carried out according to customary methods known to the person skilled in the art. Preferably, the preparation and, if appropriate, the separation of these compounds are carried out as described in EP 0 799 819 A1. The corresponding literature description is hereby inserted as reference and is thus regarded as part of the disclosure.

As salt-forming antiobesity agents, the pharmaceutical salt according to the invention can preferably contain D-norpseudoephedrine, phenylpropanolamine, amfepramone, mefenorex or ephedrine.

As salt-forming analeptics and/or antihypoxemics, the pharmaceutical salt according to the invention can preferably contain norfenefrine, heptaminol or amezinium, particularly preferably amezinium.

As salt-forming opioid antagonists, the pharmaceutical salt according to the invention can preferably contain levallorphan, naloxone or naltrexone.

As a salt-forming anthelmintic, the pharmaceutical salt according to the invention can preferably contain pyrvinium.

As salt-forming antiallergics, the pharmaceutical salt according to the invention can preferably contain reproterol, triprolidine, hydroxyzine, azelastine, diphenhydramine, promethazine, pheniramine, dexchlorpheniramine, clemastine, tramazoline, brompheniramine, dimetindene, levocabastine, doxylamine, cyproheptadine, carbinoxamine, meclozine, bamipine, chlorphenoxamine, ketotifen or cetirizine, particularly preferably diphenhydramine.

As salt-forming antiarrhythmics, the pharmaceutical salt according to the invention can preferably contain orciprenaline, aprindine, verapamil, metoprolol, quinidine, amiodarone, sotalol, propafenone, diltiazem, disopyramide, propranolol, ipatropium [sic], mexiletine, prajmaline, procainamide, gallopamil, propafenone, detajmium, flecainide, oxprenolol or tocainide, particularly preferably verapamil or diltiazem.

As salt-forming antibiotics, the pharmaceutical salt according to the invention can preferably contain vancomycin, tetracycline, clindamycin, minocycline, lincomycin, bacampicillin, amicacin, chlortetracycline, neomycin, tobramycin, netilmicin, quinine, chloroquine, ciprofloxacin, clindamycin, colistine, erythromycin, gentamicin, tobramycin [sic], cefetametpivotil, amantadine, halofantrine, saquinavir, mefloquine, framycetin, cefepime, bromhexine, cefpodoximeproxetil, oxytetracycline, proguanil, pefloxacine, polymyxin B, hydroxychloroquine, spectinomycin, sultamicillin, valaciclovir or grepafloxacin.

As salt-forming antidementive (nootropics), the pharmaceutical salt according to the invention can preferably contain butalamine, memantine, pyritinol, donepezil, moxaverine, meclofenoxate, dihydroergotoxin, viquidil, naftidrofuryl, dihydroergocornine, dihydroergocristine, benzyclan, procaine, deamol, diisopropylamine or 3-pyridylmethanol.

As a salt-forming antidiabetic, the pharmaceutical salt according to the invention can preferably contain metformin.

As salt-forming antiemetics and/or antivertiginous agents, the pharmaceutical salt according to the invention can preferably contain betahistidine, dolasetron, meclozine, hydroxycine, diphenhydramine, pyridoxine, granisetrone, triflupromazine, triethylperazine, betahistine, alizapride or odansetrone, particularly preferably diphenhydramine.

As a salt-forming antiepileptic, the pharmaceutical salt according to the invention can preferably contain tiagabine.

As salt-forming antihypertensives, the pharmaceutical salt according to the invention can preferably contain dihydralazine, prazosine, amiloride, bunazosine, nicardipine, alprenolol, candesartancilexetil, metoprolol, verapamil, propranolol, penbutolol, doxazosine, clonidine, benazepril, phenoxybenzamine, diltiazem, diisopropylamine, urapide, carteolol, guanethidine, guanfacine, terazosine, oxprenolol, cicletanine, betaxolol, nebivolol, acebutolol, enalapril or indoramine, particularly preferably verapamil or diltiazem.

As salt-forming antihypotensives, the pharmaceutical salt according to the invention can preferably contain etilefrine, pholedrine, norfenefrine, cafedrine, theodrenaline, oxilofrine, dobutamine, dopamine, phenylephrine, midodrine, heptaminol, oxedrine tartrate, pholedrine or gepefrine, particularly preferably phenylephrine.

As salt-forming antimycotics, the pharmaceutical salt according to the invention can preferably contain benzalkonium, econazole, miconazole, methyl-rosanilinium, terbinafine, amorolfine, fenticonazole, dequalinium, oxyconazole, croconazole, isoconazole or sertaconazole.

As a salt-forming antiinflammatory, the pharmaceutical salt according to the invention can preferably contain orphenadrine.

As salt-forming antitussives and/or expectorants, the pharmaceutical salt according to the invention can preferably contain ambroxole, doxycycline, bromhexine, dextromethorphan, diphenhydramine, terbutaline, chlorphenamine, eprazinone, ephedrine, chlorbutinol, pentoxyverine, pipazetate or benproperine, particularly preferably diphenhydramine.

As a salt-forming antisclerosis agent, the pharmaceutical salt according to the invention can preferably contain butalamine.

As β-receptor blockers and/or calcium channel blockers, the pharmaceutical salt according to the invention can preferably contain acebutolol, nicardipine, alprenolol, metoprolol, verapamil, enalapril, bupranolol, penbutolol, propranolol, bisoprolol, esmolol, celiprolol, benazepril, diltiazem, mepindolol, sotalol, carteolol, gallopamil or oxprenolol, particularly preferably verapamil or diltiazem.

As salt-forming broncholytics and/or antiasthmatics, the pharmaceutical salt according to the invention can preferably contain ketotifen, reproterol, orciprenaline, salbutamol, terbutaline, ephedrine, tulobuterol, ipatropium [sic], fenoterol, terbutaline [sic], formoterol, salbutamol [sic], oxytropium or pirbuterol.

As salt-forming cholinergics, the pharmaceutical salt according to the invention can preferably contain pyridostigmine, betanechol or neostigmine.

As salt-forming diuretics, the pharmaceutical salt according to the invention can preferably contain amiloride or oxprenolol.

As salt-forming, circulation-promoting agents, the pharmaceutical salt according to the invention can preferably contain butalamine, naftidrofuryl, buflomedil, moxaverine, bencyclan or meclofenoxate.

As a salt-forming weaning agent, the pharmaceutical salt according to the invention can preferably contain naltrexone, methadone, buprenorphine.

As salt-forming geriatrics, the pharmaceutical salt according to the invention can preferably contain procaine or deanolace.

As salt-forming hypnotics and/or sedatives, the pharmaceutical salt according to the invention can preferably contain promethazine, zolpidem tartrate, midazolam, melperone or flurazepam.

As a salt-forming immunomodulator, the pharmaceutical salt according to the invention can preferably contain levamisole.

As salt-forming oral and/or pharyngeal therapeutics, the pharmaceutical salt according to the invention can preferably contain chlorhexidine or cetylpyridinium.

As a salt-forming coronary agent, the pharmaceutical salt according to the invention can preferably contain oxyfedrine.

As a salt-forming hypolipidemic, the pharmaceutical salt according to the invention can preferably contain colestipol.

As salt-forming local anesthetics and/or neural therapeutics, the pharmaceutical salt according to the invention can preferably contain bupivacaine, lidocaine, mepivacaine, ropivacaine, procaine, articaine or prilocaine.

As salt-forming gastric and/or intestinal agents, the pharmaceutical salt according to the invention can preferably contain pizotifen, pirenzepine, roxatidine, ranitidine, butinoline, methanthelinium or metoclopramide.

As salt-forming migraine agents, the pharmaceutical salt according to the invention can preferably contain lisuride, methysergide, dihydroergotamine, ergotamine, sumatriptan, rizatriptan or naratriptan.

As salt-forming muscle relaxants, the pharmaceutical salt according to the invention can preferably contain alcuronium, mivacuronium, atracurium, vecurmium, pancurmium, suxamethonium, tolperisone, pridinol, orphenadrine or tizanidine.

As a salt-forming anesthetic, the pharmaceutical salt according to the invention can preferably contain ketamine or midazolam.

As a salt-forming neuropathy preparation, the pharmaceutical salt according to the invention can preferably contain thiamine.

As salt-forming ophthalmologicals and/or otologicals, the pharmaceutical salt according to the invention can preferably contain oxybuprocaine, proxymetacaine, kanamycin, tolazoline, tetryzoline, tramazoline, phenylephrine, xylomethazoli [sic], naphazoline, timolol, metipranolol, betaxolol, befunolol, levobunolol, brimonidine, clonidine, pilocarpine, dipivefrine, aceclidine, apraclonidine, neostigmine, dorzolamide, atropine, scopolamine, cyclopentolate or homatropine, particularly preferably phenylephrine.

As salt-forming Parkinson agents, the pharmaceutical salt according to the invention can preferably contain amantadine, biperidene, selegiline, bromocriptine, trihexyphenidyl, metrixene, benzaseride, lisuride, benzatropine, ropinirol, pergolide, bupidine, procyclidine, pramipexol, bomapine or tiapride.

As salt-forming psychopharmaceutical agents, the pharmaceutical salt according to the invention can preferably contain tranylcypromine, amitriptyline, doxepine, maprotiline, clomipramine, opipramol, imipramine, trimipramine, lofepramine, desipramine, dibenzepine, nortriptyline, mianserine, citalopram, fluvoxamine, fluoxetil, trazodone, paroxetin, nefazodone, sertralin, viloxacin, venlafaxine, promethazine, chlorprothixene, zuclopenthixol, pipamperone, fluphenazine, flupentixol, melperone, prothipendyl, thioridazine, levomepromazine, quetiapine, triflupromazine, perazine, fenetylline, methylphenidate, hydroxycine, buspirone, deanolace or memantine.

As salt-forming rhinologicals/sinusitis agents, the pharmaceutical salt according to the invention can preferably contain diphenylpyraline, xylometazoline, oxymetazoline, tramazoline, indanazoline, naphazoline or tetryzoline.

As salt-forming spasmolytics, the pharmaceutical salt according to the invention can preferably contain atropine, phenamazide, butylscopolaminium, propiverine, mebeverine, pipenzolate, oxybutynine, flavoxate, trospium, denaverine or glycopyrronium.

As salt-forming platelet aggregation inhibitors, the pharmaceutical salt according to the invention can preferably contain tirofiban, ticlopidine or clopidogrel.

As a salt-forming tuberculosis agent, the pharmaceutical salt according to the invention can preferably contain ethambutol.

As salt-forming urologicals, the pharmaceutical salt according to the invention can preferably contain choline, tolterodine, phenoxybenzamine, atropine, propiverine, distigmine, emepronium, tamsulosine, doxazosine, terazosine, alfuzosine, bamethane, yohimbine or sildenafil.

As salt-forming cytostatics, the pharmaceutical salt according to the invention can preferably contain aclarubicin, nimustatin, doxorubicin, bleomycin, vinblastine, vincristine, daunorubicin, decarbazine, vindesine, epirubicin, gemcitabine, procarbazil, mitoxantrone, bedamustine, idarubicin, aclarubicin [sic], irinotecan, topotecan, toremifen or tamoxifen.

The pharmaceutical salts according to the invention can be prepared according to customary methods known to the person skilled in the art. Preferably, for the preparation of the pharmaceutical salts according to the invention, at least one salt of the respective active compound and at least one salt of the respective sugar substitute are in each case dissolved separately from one another in an amount of a solvent or solvent mixture which is as small as possible, optionally with warming.

Both solutions are then combined, optionally mixed and optionally cooled. If the pharmaceutical salt according to the invention of the active compound and the sugar substitute precipitates at least partially from the optionally cooled solution, this is separated off according to customary methods, preferably by suction filtration. The pharmaceutical salt separated off is then purified, if necessary, according to customary methods known to the person skilled in the art, for example by recrystallization, washing or by stirring in a suitable solvent.

If the pharmaceutical salt has still not completely precipitated, the remaining solution is preferably concentrated completely on a rotary evaporator and the pharmaceutical salt according to the invention is extracted from the residue according to customary methods known to the person skilled in the art and purified as described above.

The solvent or solvent mixture suitable in each case for the preparation and the suitable reaction conditions, such as, for example, temperature or reaction time, can be determined by the person skilled in the art with the aid of simple preliminary tests. If both the active compound salt and the salt of the sugar substitute have an adequate solubility in water, the solvent used is preferably water. The salt of the respective active compound employed is preferably its hydrochloride, hydrobromide, phosphate, hydrogenphosphate, hydrogensulfate, sulfate, nitrate or metilsulfate. The salt of the respective sugar substitute employed is preferably its sodium, potassium, calcium or ammonium salt.

Of course, it is also possible to react the respective active compound per se with [sic] the free acid of a sugar substitute with one another in a suitable reaction medium and to isolate and, if appropriate, to purify the pharmaceutical salt thus obtained according to customary methods known to the person skilled in the art.

A further subject of the present invention are medicaments comprising at least one pharmaceutical salt according to the invention and, if appropriate, physiologically tolerable excipients. The corresponding medicaments can be used for the treatment of the indications known for the respective active compounds.

Preferably, medicaments according to the invention which contain at least one pharmaceutical salt according to the invention of a salt-forming opioid, opioid analog, ephedrine, chloroquine, lidocaine, ethaverine, preglumetacin or triflupromaazine or a salt-forming compound of the general formula I, II, III or IV indicated above and a sugar substitute are employed for the control of pain. Preferably, the medicaments according to the invention contain the corresponding saccharinates as pharmaceutical salts of these active compounds.

For the treatment of urinary incontinence, medicaments according to the invention are preferably employed which contain at least one pharmaceutical salt of a salt-forming compound of the general formula I, II, III or IV indicated above, or a compound from the group consisting of oxybutymine, tolterodine, propiverine and trospium and a sugar substitute. Preferably, the medicaments according to the invention contain the corresponding saccharinates as pharmaceutical salts of these active compounds.

The medicaments according to the invention can be present in solid, semisolid or liquid form. Preferably, the medicaments according to the invention are suitable for oral administration.

In a preferred embodiment, the medicament according to the invention is present formulated as a gel, chewing gum, juice, spray, tablet, chewable tablet, coated tablet, powder, if appropriate filled into capsules, easily reconstitutable dry preparations, preferably as a gel, as an aqueous or oily juice, as a sublingual spray, tablets or chewable tablets.

Likewise preferably, the medicament according to the invention can also be present formulated in multiparticulate form, preferably in the form of microtablets, microcapsules, granules, active compound crystals or pellets, particularly preferably in the form of microtablets, granules or pellets, optionally filled into capsules or compressed to give tablets.

If the medicament according to the invention is present in the form of granules or pellets, these can preferably have a size in the range from 0.1 to 3 mm, particularly preferably in the range from 0.5 to 2 mm.

If the medicament according to the invention is present in the form of microtablets, these can preferably have a diameter in the range from 0.5 to 5 mm, particularly preferably in the range from 1 to 3 mm and very particularly preferably in the range from 1 to 2 mm.

If the medicament according to the invention is present in the form of active compound crystals, microparticles, micropellets or microcapsules, these can preferably have a diameter in the range from 10 µm to 1 mm, particularly preferably in the range from 15 µm to 0.5 mm and very particularly preferably in the range from 30 µm to 200 µm.

Depending on embodiment, the medicaments according to the invention can moreover contain the customary physiologically tolerable excipients known to the person skilled in the art as further constituents.

If the medicaments according to the invention are present in the form of tablets or microtablets, these can be present as physiologically tolerable excipients, preferably microcrystalline cellulose, cellulose ethers, lactose, starch, starch derivatives, sugar alcohols, calcium hydrogenphosphate and the customary binders, flow regulators, lubricants and/or disintegrants known to the person skilled in the art.

If the medicaments according to the invention are present in the form of gels or chewing gums, these can preferably contain methylparaben, propylparaben, xylitol and/or xanthan gum as physiologically tolerable excipients.

If the medicaments according to the invention are present in the form of pellets, granules or micropellets, these can preferably contain microcrystalline cellulose, cellulose ethers, lactose, starch and starch derivatives, sugar alcohols, calcium hydrogenphosphate, fatty alcohols, esters of glycerol or fatty acid esters as physiologically tolerable excipients.

If the medicaments according to the invention are present in the form of microcapsules or microparticles, these can contain, depending on the nature of the process employed for their preparation, the customary physiologically tolerable excipients known to the person skilled in the art.

The medicaments according to the invention can be prepared by customary methods known to the person skilled in the art.

If the medicaments according to the invention are present in the form of tablets, preferably the pharmaceutical salt according to the invention and, if appropriate, the physiologically tolerable excipients are preferably mixed homogeneously with one another, processed to give granules by means of moist, dry or melt granulation and compressed to give tablets or produced by direct tableting of the pharmaceutical salt with further excipients. In addition, the tablets can preferably be produced by compression of optionally coated pellets, active compound crystals, microparticles or microcapsules.

The medicaments according to the invention in the form of pellets can preferably be produced by mixing the pharmaceutical salt and physiologically tolerable excipients, extrusion and spheronization, by build-up pelletization or by direct pelletization in a high-speed mixer or in the rotor fluidized bed. The pellets are particularly preferably prepared by extrusion of moist masses and subsequent spheronization.

Microcapsules are prepared according to customary microencapsulation processes, such as, for example, by spray drying, spray solidification or coacervation.

The medicaments according to the invention in semisolid form, such as, for example, gels or chewing guns, are preferably suitable for the administration of the pharmaceutical salt according to the invention via the oral mucosa, the medicaments according to the invention in solid or liquid form, such as, for example, oily or aqueous juices, tablets or multiparticulate forms are preferably suitable for the administration of the pharmaceutical salt according to the invention via the gastric tract. If the absorption of active compound from the medicament according to the invention in solid form is only intended via the gastric tract, they must have at least one enteric coating. This enteric coating enables them to pass through the gastric tract undissolved and the pharmaceutical salt is only released in the intestinal tract. Preferably, the enteric coating dissolves at a pH of between 5 and 7.5.

The medicament according to the invention can contain the pharmaceutical salt according to the invention also partially or completely in delayed-release form.

The delaying of the release of active compound is preferably based on the application of a release-delaying coating, on embedding in a release-delaying matrix, binding to an ion-exchange resin or on a combination of these abovementioned release-delaying methods.

Preferably, the release-delaying coating is based on a water-insoluble, optionally modified natural or synthetic polymer or on a natural, semisynthetic or synthetic wax or fat or fatty alcohol or a mixture of at least two of these abovementioned components.

Water-insoluble polymers employed for the preparation of a release-delaying coating are preferably poly(meth) acrylates, particularly preferably poly($C_{1-4}$) alkyl (meth)acrylates, poly($C_{1-4}$)dialkylamino-($C_{1-4}$)-alkyl (meth)acrylates and/or their copolymers, very particularly preferably ethyl acrylate/methyl methacrylate copolymers having a molar ratio of the monomers of 2:1, ethyl acrylate/methyl methacrylate/trimethylammonium ethyl methacrylate chloride copolymers having a molar ratio of the monomers of 1:2:0.1, ethyl acrylate/methyl methacrylate/trimethylammonium ethyl methacrylate chloride copolymers having a molar ratio of the monomers of 1:2:0.2 or a mixture of at least two of these abovementioned polymers as a coating material.

These coating materials are obtainable on the market as 30% strength by weight aqueous latex dispersions under the names Eudragit RS30D®, Eudragit NE30D® and Eudragit RL30D® and are preferably also employed as a coating material as such.

Likewise preferably, the water-insoluble polymers employed for the preparation of the release-delaying coating for the medicaments according to the invention can be polyvinyl acetates, optionally in combination with further excipients. These are obtainable on the market as an aqueous dispersion containing 27% by weight of polyvinyl acetate, 2.5% by weight of povidone and 0.3% by weight of sodium lauryl sulphate (Kollicoat SR 30 D®).

In a further preferred embodiment, the release-delaying coatings of the medicaments according to the invention are based on water-insoluble cellulose derivatives, preferably alkylcelluloses, such as, for example, ethylcellulose, or on cellulose esters, such as, for example, cellulose acetate, as a coating material. The coatings of ethylcellulose or cellulose acetate are preferably applied from aqueous pseudolatex dispersion. Aqueous ethylcellulose-pseudolatex dispersions are stocked on the market as 30% strength by weight dispersions (Aquacoat®) or as 25% strength by weight dispersions (Surelease®) and as such are preferably also employed as a coating material.

As natural, semisynthetic or synthetic waxes, fats or fatty alcohols, the release-delaying coating in the medicament according to the invention can preferably contain carnauba wax, beeswax, glycerol monostearate, glycerol monobehenate (Compritol ATO888®), glycerol ditripalmitostearate (Precirol AT05®), microcrystalline wax, cetyl alcohol, cetylstearyl alcohol, or a mixture of at least two of these components.

If the release-delaying coating is based on a water-insoluble, optionally modified natural and/or synthetic polymer, the coating dispersion or solution can contain, in addition to the corresponding polymer, a customary physiologically tolerable plasticizer known to the person skilled in the art in order to lower the minimum film temperature necessary.

Suitable plasticizers are, for example, lipophilic diesters of an aliphatic or aromatic dicarboxylic acid of $C_6$-$C_{40}$ and an aliphatic alcohol of $C_1$-$C_8$, such as, for example, dibutyl phthalate, diethyl phthalate, dibutyl sebacate or diethyl sebacate, hydrophilic or lipophilic esters of citric acid, such as, for example, triethyl citrate, tributyl citrate, acetyltributyl citrate or acetyltriethyl citrate, polyalkylene glycols, such as, for example, polyethylene glycols or propylene glycols, esters of glycerol, such as, for example, triacetin, Myvacet® (acetylated mono- and diglycerides, $C_{23}H_{44}O_5$ to $C_{25}H_{47}O_7$), medium-chain triglycerides (Miglyol®), oleic acid or mixtures of at least two of the abovementioned plasticizers.

Preferably, aqueous dispersions of Eudragit RS® and optionally Eudragit RL® contain triethyl citrate as a plasticizer.

Preferably, the release-delaying coating contains the plasticizer(s) in amounts of 5 to 50% by weight, particularly preferably 10 to 40% by weight and very particularly preferably 10 to 30% by weight, based on the amount of the polymer employed.

In individual cases, for example for cellulose acetate, higher amounts of plasticizers, preferably up to 110% by weight, based on the amount of cellulose acetate, can also be employed.

In addition, the release-delaying coating can contain further customary excipients known to the person skilled in the art, such as, for example, lubricants, preferably talc or glycerol monostearate, color pigments, preferably iron oxides or titanium dioxide, or surfactants, such as, for example, Tween 80®.

The release profile of the delayed active compound component can be adjusted by the customary methods known to the person skilled in the art, such as, for example, by the thickness of the coating or by the use of further excipients as constituents of the coating. Suitable excipients are, for example, hydrophilic or pH-dependent pore-forming agents, such as, for example, sodium carboxymethylcellulose, cellulose acetate phthalate, hydroxypropylmethylcellulose acetate succinate, lactose, polyethylene glycol or mannitol or water-soluble polymers, such as, for example, polyvinylpyrrolidone or water-soluble celluloses, preferably hydroxypropylmethylcellulose or hydroxypropylcellulose.

The release-delaying coating can also contain insoluble or lipophilic excipients, such as, for example, alkylized silicone, which is stocked on the market, for example, as Aerosil R972®, or magnesium stearate for the further intensification of the delaying.

The respective formulation of the medicament according to the invention can optionally also contain, in addition to the release-delaying coating, at least one further coating. This can be, for example, a coating for improving the taste or an enteric coating.

The enteric coating is preferably based on methacrylic acid/methyl methacrylate copolymers having a molar ratio of the respective monomers of 1:1 (Eudragit L®), methacrylic acid/methyl methacrylate copolymers having a molar ratio of the respective monomers of 1:2 (Eudragit S®), methacrylic acid/ethyl acrylate copolymers having a molar ratio of the respective monomers of 1:1 (Eudragit L30D-55®), methacrylic acid/methyl acrylate/methyl methacrylate copolymers having a molar ratio of the respective monomers of 7:3:1 (Eudragit FS®), shellac hydroxypropylmethylcellulose acetate succinate, cellulose acetate phthalate or a mixture of at least two of these abovementioned components, which can optionally also be employed in combination with the abovementioned water-insoluble poly(meth) acrylates, preferably in combination with Eudragit NE30D® and/or Eudragit RL® and/or Eudragit RS®.

The coatings can be applied by customary processes suitable for the respective coating and known to the person skilled in the art, such as, for example, by spraying on solutions, dispersions or suspensions, by melt processes or by powder application processes. The solutions, dispersions or suspensions can be employed in the form of aqueous and/or organic solutions or dispersions. In this context, aqueous dispersions are preferably employed. Organic solvents which can preferably be used are alcohols, for example ethanol or isopropanol, ketones, such as, for example, acetone, esters, for example ethyl acetate, chlorinated hydrocarbons, such as, for example, dichloromethane, with alcohols or ketones being particularly preferably employed. It is also possible to employ mixtures of at least two of the abovementioned solvents.

If the medicament is present in multiparticulate form and the active compound is to be released at least partially in delayed form, the release-delaying coating is preferably applied such that the multiparticulate forms comprising the active compound salt are coated after their preparation with the corresponding polymers and, if appropriate, another active compound and/or the same active compound salt and, if appropriate, further physiologically tolerable excipients from aqueous and/or organic media, preferably from aqueous media, with the aid of the fluidized bed process and the coating is preferably simultaneously dried in the fluidized bed at customary temperatures and, if appropriate, annealed if necessary.

Preferably, the drying of the coating is carried out for poly(meth)acrylate coatings at a feed air temperature in the range from 30 to 50°, particularly preferably in the range from 35 to 45° C.

For coatings based on cellulose, such as, for example, ethylcellulose or cellulose acetate, the drying is preferably carried out at a temperature in the range from 50 to 80° C., particularly preferably in the range from 55 to 65° C.

Wax coatings can be applied by melt coating in the fluidized bed and cooled at temperatures below the respective melt range after the coating for complete solidification. The application of wax coatings can also be carried out by spraying on their solutions in organic solvents.

For the modification of the active compound release profile, the medicament according to the invention can contain the pharmaceutical salt whose release is to be delayed also in a release-delaying matrix, preferably uniformly dispersed.

Matrix materials which can be used are physiologically tolerable, hydrophilic materials which are known to the person skilled in the art. Preferably, the hydrophilic matrix materials used are polymers, particularly preferably cellulose ethers, cellulose esters and/or acrylic resins. Very particularly preferably, the matrix materials employed are ethylcellulose, hydroxypropylmethylcellulose, hydroxypropylcellulose, hydroxymethylcellulose, poly(meth)acrylic acid and/or their derivatives, such as, for example, their salts, amides or esters.

Likewise preferred are matrix materials made of hydrophobic materials, such as hydrophobic polymers, waxes, fats, long-chain fatty acids, fatty alcohols or appropriate esters or ethers or mixtures of at least two of the abovementioned materials. Particularly preferably, the hydrophobic materials employed are mono- or diglycerides of $C_{12}$-$C_{30}$-fatty acids and/or $C_{12}$-$C_{30}$-fatty alcohols and/or waxes or mixtures of at least two of the abovementioned materials.

It is also possible to employ mixtures of the abovementioned hydrophilic and hydrophobic materials as a release-delaying matrix material.

The release-delaying matrix can be prepared by the customary methods known to the person skilled in the art.

A further subject of the invention is also the use of at least one pharmaceutical salt according to the invention and, if appropriate, physiologically tolerable excipients for the production of a medicament. The corresponding medicaments can be used for the treatment of the indications known for the respective active compounds.

Preferred is the use of at least one pharmaceutical salt of a salt-forming opioid, opioid analog, ephedrine, chloroquine, lidocaine, ethaverine, preglumetacin, truflupromazine or a salt-forming compound of the general formula I, II, III or IV indicated above for the production of a medicament for the control of pain, the salts of these active compounds used preferably being their saccharinates.

Likewise preferred is the use of at least one pharmaceutical salt of a salt-forming compound of the general formula I, II, III or IV indicated above for the production of a medicament for the treatment of urinary incontinence, the salts of these active compounds used preferably being their saccharinates.

The total amount of the respective pharmaceutical salt to be administered to the patient varies, for example, depending on the the weight of the patient, on the indication and the degree of severity of the pain or of the disorder. It is known to the person skilled in the art on account of the properties of the respective active compounds in what doses these are to be administered in order to achieve the desired effect.

The pharmaceutical salts according to the invention of a pharmaceutical active compound and a sugar substitute are distinguished compared with the conventionally used salts of these active compounds customarily by a lower solubility in water. Preferably, these are the saccharinates of the respective active compounds, whose water solubility is usually ≤250 mg/ml and, compared with the water solubility of the conventional salts of the corresponding active compound, is usually lowered by at least 50%.

By this means, the formulation of these pharmaceutical salts to give medicaments, for example the preparation of granules by extrusion, is also simplified. On account of the altered solubility, the pharmaceutical salts according to the invention further enable more effective release-delaying of the active compound using customary delaying processes in comparison to salts customarily used. Delayed-release medicaments which contain these pharmaceutical salts according to the invention can therefore be produced more simply and more inexpensively. This also applies for other modifications of the medicaments according to the invention, such as, for example, with enteric coatings.

From the medicaments according to the invention, which are employed for the administration of the respective pharmaceutical salt via the oral mucosa or the gastric tract, a largely controlled release of the respective active compound without the use of a release-delaying matrix and/or a release-delaying coating, but if appropriate with an enteric coating, is moreover achieved.

The medicaments according to the invention in the form to be administered orally, which release the respective active compound as early as on or immediately after administration, furthermore have the advantage that their strongly bitter or nauseating taste is compensated by the simultaneous release of the sugar substitute. The adherence to the dosage instructions in the patients thereby improves and the medicaments which contain the respective active compound as a salt experience a greater acceptance. The medicaments according to the invention are moreover also suitable for diabetics.

For a large number of the abovementioned active compounds, the water solubility of the conventional active compound salts is known, for example from Pharmazeutische Stoffliste [Pharmaceutical Substance List], 12th edition ABDATA Pharma-Daten-Service, 65735 Eschborn/

Taunus. The corresponding disclosure [sic] is hereby inserted as reference and is thus regarded as part of the disclosure.

If the water solubility of an active compound salt is not known, it can be determined according to the method indicated below, according to which the water solubility of the pharmaceutical salts according to the invention has also been determined:

In a clear colorless vessel made of transparent material, such as, for example, glass or plastic, 1 ml of ion-free water or a fraction (amount A in ml) thereof is introduced at a temperature of 20° C. While stirring with a magnetic stirrer rod, the conventional active compound salt to be tested or the pharmaceutical salt according to the invention was then added in portions.

If the amount of salt B added (in mg) completely dissolved, further amounts of the respective salt were slowly added. Each further addition was recorded and the solution behavior observed. As soon as the first turbidity due to undissolved salt was found by observation against a suitable background, stirring was continued for a further 10 minutes. If undissolved constituents subsequently remained, the sum C (in mg) of the amount of substance employed was determined. If a clear solution resulted again on stirring, further small amounts of the respective salt were added and the mixture was in each case stirred again for 10 minutes until a first turbidity remained on account of undissolved salts. The excess amount of undissolved substance was then brought into solution with stirring by addition of small amounts of water. After a clear solution had been obtained, the sum D (in ml) of the amount of water employed was determined. The solubility of the respective salt per 1 ml of water was then calculated according to the following formula:

$$\text{Water solubility of the active compound salt in mg/ml of water} = \frac{(C/A) + (C/D)}{2}$$

If the amount B added (in mg) of the respective salt did not dissolve immediately and a turbidity resulted, after the addition of the salt the mixture was stirred for a further 10 minutes. If undissolved salt still remained then, the undissolved portion was brought into solution by addition of small amounts of water with stirring. After obtainment of a clear solution, the sum E (in ml) of the amounts of water employed was determined. The solubility of the respective salt per 1 ml of water was then calculated according to the following formula:

$$\text{Water solubility of the active compound salt in mg/ml of water} = \frac{B}{E}$$

The invention is explained below with the aid of examples. These explanations are only by way of example and do not restrict the general inventive concept.

EXAMPLES

Example 1

The preparation and the subsequent separation of the optically pure compound (+)-(1S,2S)-3-(3-dimethylamino-1-ethyl-2-methylpropyl)phenol was carried out according to DE-A-4426245. The corresponding part of the disclosure [sic] is hereby inserted as reference and is thus regarded as part of the disclosure.

For the preparation of (+)-(1S,2S)-3-(3-dimethylamino-1-ethyl-2-methylpropyl)phenol saccharinate, 2.58 g (10 mmol) of (+)-(1S,2S)-3-(3-dimethylamino-1-ethyl-2-methylpropyl)phenol hydrochloride and 2.42 g (10 mmol) of saccharin-sodium dihydrate were in each case completely dissolved with warming in an amount of water which was as small as possible. Both solutions were then mixed with one another with stirring and then placed in a cool place overnight. The precipitated (+)-(1S,2S)-3-(3-dimethylamino-1-ethyl-2-methylpropyl) phenol saccharinate was separated off from the supernatant mother liquor, purified with ethanol and isolated according to conventional methods.

Example 2

For the preparation of diphenhydramine saccharinate, 5.0 g (17.1 mmol) of diphenhydramine hydrochloride and 4.13 g (17.1 mmol) of saccharin-sodium dihydrate were in each case completely dissolved with warming in an amount of water which was as small as possible. Both solutions were then mixed with one another with stirring and then placed in a cool place overnight. The precipitated diphenhydramine saccharinate was separated off from the supernatant mother liquor, purified with ethanol and isolated according to conventional methods.

Example 3

For the preparation of verapamil saccharinate, 415 mg (0.845 mmol) of verapamil hydrochloride and 204 mg (0.845 mmol) of saccharin-sodium dihydrate were in each case completely dissolved with warming in an amount of water which was as small as possible. Both solutions were then mixed with one another with stirring and then placed in a cool place overnight. The precipitated verapamil saccharinate was separated off from the supernatant mother liquor, purified with ethanol and isolated according to conventional methods.

Example 4

For the preparation of morphine saccharinate, 285 mg (0.76 mmol) of morphine hydrochloride trihydrate and 183 mg (0.76 mmol) of saccharin-sodium dihydrate were in each case completely dissolved with warming in an amount of water which was as small as possible. Both solutions were then mixed with one another with stirring and then placed in a cool place overnight. The precipitated morphine saccharinate was separated off from the supernatant mother liquor, purified with ethanol and isolated according to conventional methods.

Example 5

For the preparation of an oral gel, 0.33 g of methylparaben, 0.05 g of propylparaben and 75.0 g of xylitol were first dissolved in 198.0 g of purified water at a temperature of 80° C. and the mixture was then cooled to 40° C. Then, initially 0.94 g of diphenhydramine saccharinate obtained according to example 2 and subsequently 2 g of xanthan gum were added with stirring, stirring was continued for one hour and evaporated water was replaced. After cooling to a temperature of 20 to 25° C., the mixture was flavored with 0.625 g of Tutti-Frutti 9/008897 (Dragoco Gerberding & Co. AG, 37603 Holzminden) while stirring.

Example 6

5 g of comminuted chewing gum mass (Popeye Amural Confections, Yorkville, Ill., USA) were warmed to a temperature of 30 to 40° C. in a Fanta dish. 187.9 mg of diphenhydramine saccharinate obtained according to example 2 were then incorporated into the viscous chewing gum mass using a pestle. The homogeneous mass was then portioned into teflonized molds to give portions of 1 g each.

The taste test showed that the chewing gums which contained the diphenhydramine saccharinate had an excellent taste at the start and were still enjoyable even after a relatively long chewing time.

Example 7

For the preparation of a juice on an aqueous basis, 0.33 g of methylparaben, 0.05 g of propylparaben and 75.0 g of xylitol were dissolved in 199.22 g of purified water at a temperature of 80° C. The mixture was cooled to 40° C. and 78.5 mg of (+)-(1S,2S)-3-(3-dimethylamino-1-ethyl-2-methylpropyl)phenol saccharinate obtained according to example 1 were added with stirring. 0.25 g of xanthan gum was then added, stirring was continued for one hour and evaporated water was replaced. After cooling to [lacuna] temperature of 20 to 25° C., the mixture was flavored while stirring with 0.075 g of orange-mandarin flavor 10888-56 (Givaudan Roure Flavors Ltd. CH 8600 Dübendorf).

Example 8

In this example, the water solubility of certain pharmaceutical salts and of conventional salts of the corresponding active compound was determined according to the method indicated above. The solubility values thus obtained are presented in table 1 below:

TABLE 1

Comparison of the water solubilities of certain pharmaceutical salts according to the invention and corresponding conventional salts of these active compounds. The conventional salt employed in each case is indicated in brackets.

| Active compound | Solubility of the active compound salt in mg/ml of water | Solubility of the active compound saccharinate in mg/ml of water |
| --- | --- | --- |
| (−)-(1R,2R)-3-(3-dimethylamino-1-ethyl-2-methylpropyl)phenol | 261 (hydrochloride) | 31 |
| (1RS,3RS,6RS)-6-dimethylaminomethyl-1-(3-methoxy-phenyl)cyclohexane-1,3-diol [sic] | 500 (hydrochloride) | 71 |
| (+)-(1S,2S)-3-(3-dimethylamino-1-ethyl-2-methylpropyl)phenol | 650 (hydrochloride) | 55 |
| (−)-(1S,2S)-3-(3-dimethylamino-1-ethyl-1-fluoro-2-methyl-propyl)phenol | 568 (hydrochloride) | 130 |
| (−)-(2S,3S)-1-dimethylamino-3-(3-methoxyphenyl)-2-methylpentan-3-ol | 2000 (hydrochloride) | 90 |

TABLE 1-continued

Comparison of the water solubilities of certain pharmaceutical salts according to the invention and corresponding conventional salts of these active compounds. The conventional salt employed in each case is indicated in brackets.

| Active compound | Solubility of the active compound salt in mg/ml of water | Solubility of the active compound saccharinate in mg/ml of water |
| --- | --- | --- |
| (+)-(1R,2R,4S)-2-dimethylaminomethyl-4-(4-fluorobenzyl-oxy)-1-(3-methoxy-phenyl)cyclohexanol | 33 (hydrochloride) | 10 |
| Morphine | 52 (hydrochloride trihydrate) | 25 |
| Amezinium | 25 (metilsulfate) | 8 |
| Phenylephrine | 1250 (hydrochloride) | 380 |
| Verapamil | 200 (hydrochloride) | 7 |
| Diphenhydramine | 1000 (hydrochloride) | 7 |
| Benzalkonium | 500 (hydrochloride) | <2 |
| Codeine | 250 (phosphate hemihydrate) | 200 |
| Hydromorphone | 330 (hydrochloride) | 130 |
| Buprenorphine | 14 (hydrochloride) | 2 |

As can be seen from the solubility values according to table 1, the solubility of the respective active compound saccharinates is lowered compared with the corresponding conventional active compound salts.

The invention claimed is:

1. A pharmaceutical composition comprising a delayed-release formulation of a therapeutically effective amount of a pharmaceutical salt and one or more physiologically tolerable excipients, wherein the pharmaceutical salt is selected from the group consisting of:
   (a) (−)-(1R,2R)-3-(3-Dimethylamino-1-ethyl-2-methyl-propyl)-phenol saccharinate;
   (b) (1RS,3RS,6RS)-6-Dimethylaminomethyl-1-(3-methoxy-phenyl)-cyclohexane-1,3-diol saccharinate; and
   (c) (−)-(1R,2R)-3-(2-Dimethylaminomethyl-cyclohexyl)-phenol saccharinate.

2. The pharmaceutical composition according to claim 1, wherein the pharmaceutical salt is (−)-(1R,2R)-3-(3-Dimethylamino-1-ethyl-2-methyl-propyl)-phenol saccharinate.

3. The pharmaceutical composition according to claim 1, wherein the pharmaceutical salt is (1RS,3RS,6RS)-6-Dimethylaminomethyl-1-(3-methoxy-phenyl)-cyclohexane-1,3-diol saccharinate.

4. The pharmaceutical composition according to claim 1, wherein the pharmaceutical salt is (−)-(1R,2R)-3-(2-Dimethylaminomethyl-cyclohexyl)-phenol saccharinate.

5. The pharmaceutical composition according to claim 1, which comprises one or more of the following release-delaying methods:
   (a) a release-delaying coating; or
   (b) the pharmaceutical salt embedded in a release-delaying matrix; or (c) the pharmaceutical salt bound to an ion-exchange resin.

6. The pharmaceutical composition according to claim 1, which is formulated as a tablet other than a chewable tablet, or as a capsule.

7. The pharmaceutical composition according to claim 6, which is formulated as a tablet other than a chewable tablet.

8. The pharmaceutical composition according to claim 6, which is formulated as a capsule.

9. A method of controlling pain comprising administering to a patient in need thereof a pain-controlling effective amount of the pharmaceutical composition of claim 1.

10. A method of controlling urinary incontinence comprising administering to a patient in need thereof an urinary incontinence-controlling effective amount of the pharmaceutical composition of claim 1.

\* \* \* \* \*